（12）United States Patent
El Haddad et al.

(10) Patent No.: US 10,758,141 B2
(45) Date of Patent: Sep. 1, 2020

(54) CARDIAC ACTIVATION TIME DETECTION

(71) Applicant: Biosense Webster (Israel) Ltd., Yokneam (IL)

(72) Inventors: Milad Abbas El Haddad, Ghent (BE); Gal Hayam, Tivon (IL); Meir Bar-Tal, Haifa (IL); Richard Petrus Maria Houben, Lanaken (BE); Mattias Francis Duytschaever, Drongen (BE)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/355,275

(22) Filed: Nov. 18, 2016

(65) Prior Publication Data

US 2018/0140212 A1 May 24, 2018
US 2019/0192026 A9 Jun. 27, 2019

Related U.S. Application Data

(63) Continuation of application No. 13/453,249, filed on Apr. 23, 2012, now Pat. No. 9,833,157.

(51) Int. Cl.
*A61B 5/0402* (2006.01)
*A61B 5/04* (2006.01)
*A61B 5/042* (2006.01)
*A61B 5/0452* (2006.01)
(Continued)

(52) U.S. Cl.
CPC .......... *A61B 5/04028* (2013.01); *A61B 5/042* (2013.01); *A61B 5/04011* (2013.01); *A61B 5/04012* (2013.01); *A61B 5/04014* (2013.01); *A61B 5/0452* (2013.01); *A61B 5/0456* (2013.01); *A61B 5/7239* (2013.01)

(58) Field of Classification Search
None
See application file for complete search history.

(56) References Cited

U.S. PATENT DOCUMENTS 7,218,960 B1 * 5/2007 Min ..................... A61B 5/0452
600/509
7,225,015 B1 5/2007 Min et al.
7,672,722 B1 3/2010 Mengotto
(Continued)

FOREIGN PATENT DOCUMENTS

EP 1647301 A1 4/2006
EP 2591721 A1 5/2013
(Continued)

OTHER PUBLICATIONS

Examination Report for European Patent Application No. 13164723.2 dated Apr. 21, 2017.
(Continued)

*Primary Examiner* — Erica S Lee

(57) ABSTRACT

A method for characterizing an electrocardiogram, including receiving a first unipolar signal from a first location of a heart and a second unipolar signal from a second location of the heart. The method further includes generating a bipolar signal from the first and second unipolar signals, and analyzing the bipolar signal to delineate a time period during which the first and second locations generate a bipolar complex. The method also includes analyzing the first unipolar signal within the time period to determine an activation time of the first location.

12 Claims, 11 Drawing Sheets

(51) Int. Cl.
  *A61B 5/00* (2006.01)
  *A61B 5/0456* (2006.01)

(56) References Cited

U.S. PATENT DOCUMENTS

| | | | |
|---|---|---|---|
| 7,912,535 B2 | 3/2011 | Couderc et al. | |
| 2005/0038478 A1* | 2/2005 | Klepfer | A61N 1/3622 607/9 |
| 2005/0059897 A1 | 3/2005 | Snell et al. | |
| 2008/0048742 A1* | 2/2008 | Kawai | H03L 7/093 327/158 |
| 2009/0099468 A1* | 4/2009 | Thiagalingam | A61B 5/0452 600/515 |
| 2009/0299424 A1 | 12/2009 | Narayan | |
| 2010/0094274 A1 | 4/2010 | Narayan et al. | |
| 2010/0268059 A1 | 10/2010 | Ryu et al. | |
| 2010/0274150 A1* | 10/2010 | Harlev | A61B 5/0422 600/523 |
| 2012/0101398 A1* | 4/2012 | Ramanathan | A61B 5/04012 600/523 |
| 2013/0123652 A1 | 5/2013 | Rubinstein | |
| 2013/0281870 A1* | 10/2013 | El Haddad | A61B 5/0452 600/509 |

FOREIGN PATENT DOCUMENTS

| | | |
|---|---|---|
| JP | 63-099840 A | 5/1988 |
| WO | 2005072237 A2 | 8/2005 |
| WO | 2008065412 A2 | 6/2008 |
| WO | 2010123637 A2 | 10/2010 |

OTHER PUBLICATIONS

Search Report for Chinese Patent Application No. 201310142932.5 dated Apr. 27, 2017.
Official Action for Chinese Patent Application No. 201310142932.5 dated May 8, 2017.
Gjin Ndrepepa M D D Ph et al: "Activation Time Determination by High-Resolution Unipolar and Bipolar Extracellular Electrograms in the Canine Heart Activation Time Determination by High-Resolution Electrograms. Introduction", Journal of Cardiovascular Electrophysiology Vat. No. J, Mar. 1, 1995 (Mar. 1, 1995), XP055194489, [retrieved on Jun. 9, 2015].
Chinese Search Report for Chinese corresponding application No. CN 201310142932.5, dated Dec. 12, 2016.
Chinese Office Action for Chinese corresponding application No. CN 201210142932.5, dated Dec. 23, 2016.
Zhou Yifeng et al. Comparison of Unipolar and Bipolar Electrocardiograms, Practical Medical Magazine, vol. 23, Issue 1, 2007; p. 359-360.
Chinese Search Report for CN201310142932.5 dated Mar. 2016.
Chinese Office Action for CN201310142932.5 dated Apr. 2016.
European Search Report Completed July 8, 2013 for Corresponding Patent Application No. EP13164723.
Japanese Office Action for corresponding Japanese patent application No. 2013-089158, dated Jan. 31, 2017.

* cited by examiner

CARDIAC ACTIVATION TIME DETECTION

This Application is a Continuation patent application of U.S. patent application Ser. No. 13/453,249 filed Apr. 23, 2012

FIELD OF THE INVENTION

The present invention relates generally to signal analysis, and specifically to analysis of signals generated by a beating heart.

BACKGROUND OF THE INVENTION

One of the methods for characterizing cardiac activity relies on analyzing electrical signals generated by a heart as the heart beats. The signals typically have a relatively low level, of the order of millivolts, so that accurate analysis of the signals may be difficult. Notwithstanding the difficulties, accurate analysis can lead to improved characterization of heart activity, including determination of regions of the heart which may be defective.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a method for characterizing an electrocardiogram, including:

receiving a first unipolar signal from a first location of a heart and a second unipolar signal from a second location of the heart;

generating a bipolar signal from the first and second unipolar signals;

analyzing the bipolar signal to delineate a time period during which the first and second locations generate a bipolar complex; and analyzing the first unipolar signal within the time period to determine an activation time of the first location.

Typically, analyzing the bipolar signal includes determining search window bounds to be applied to the bipolar signal. Analyzing the first unipolar signal may include applying the search window bounds to the first unipolar signal.

In a disclosed embodiment delineating the time period includes feeding data of the bipolar signal into a two-state state machine so as to determine bounds of the time period.

In a further disclosed embodiment analyzing the bipolar signal includes sorting data of the bipolar signal to determine a threshold level for the bipolar complex.

In a yet further disclosed embodiment analyzing the bipolar signal includes differentiating then rectifying data of the bipolar signal, so as to generate differentiated data. Delineating the time period may include feeding the differentiated data into a four-state state machine so as to determine bounds of the time period. Determining the activation time may include forming a first derivative of the first unipolar signal, and assigning a unipolar onset activation time as a time instant wherein the first derivative is a minimum value.

In an alternative embodiment the activation time includes a first activation time, and the method further includes analyzing the second unipolar signal within the time period to determine a second activation time of the second location.

In a further alternative embodiment the bipolar complex includes a first bipolar complex and a second bipolar complex, and the time period includes a first time period during which the first bipolar complex is generated and a second time period during which the second bipolar complex is generated, and analyzing the first unipolar signal includes determining first and second activation times respectively within the first and second time periods.

There is further provided, according to an embodiment of the present invention, apparatus for characterizing an electrocardiogram, including:

a probe which is configured to receive a first unipolar signal from a first location of a heart and a second unipolar signal from a second location of the heart; and a processor which is configured to:

generate a bipolar signal from the first and second unipolar signals, analyze the bipolar signal to delineate a time period during which the first and second locations generate a bipolar complex, and analyze the first unipolar signal within the time period to determine an activation time of the first location.

There is further provided, according to an embodiment of the present invention, a computer software product for characterizing an electrocardiogram, including a tangible computer-readable medium in which computer program instructions are stored, which instructions, when read by a computer, cause the computer to:

receive a first unipolar signal from a first location of a heart and a second unipolar signal from a second location of the heart;

generate a bipolar signal from the first and second unipolar signals;

analyze the bipolar signal to delineate a time period during which the first and second locations generate a bipolar complex; and analyze the first unipolar signal within the time period to determine an activation time of the first location.

The present disclosure will be more fully understood from the following detailed description of the embodiments thereof, taken together with the drawings, in which:

DETAILED DESCRIPTION OF EMBODIMENTS

Overview

An embodiment of the present invention provides a method for characterizing an electrocardiogram, by processing electrocardiogram data in two stages. The data is in the form of two unipolar signals from two different locations in the heart, and the characterization is able to determine activation times of locations in the heart providing the data.

In a first stage of the process, the data is analyzed as a bipolar signal, to determine time instances of the signal that delineate a bipolar complex within signal. In a second stage of the process, the time instances are used as bounds within which each of the unipolar signals may be separately analyzed.

In order to determine the activation times of the different locations, a first derivative of each of the unipolar signals is evaluated. The time at which the first derivative is a minimum is assumed to be an onset activation time, i.e., the time at which tissue generating the unipolar signal begins to activate. The method may be used to find the onset activation times of each of the two different locations.

The method may be used to analyze signals which have one bipolar complex per heart beat, and may also be used to analyze signals having more than one bipolar complex per heart beat.

The inventors have operated the method in real time, and have clinically verified that the method provides accurate results.

System Description

Figure 1:
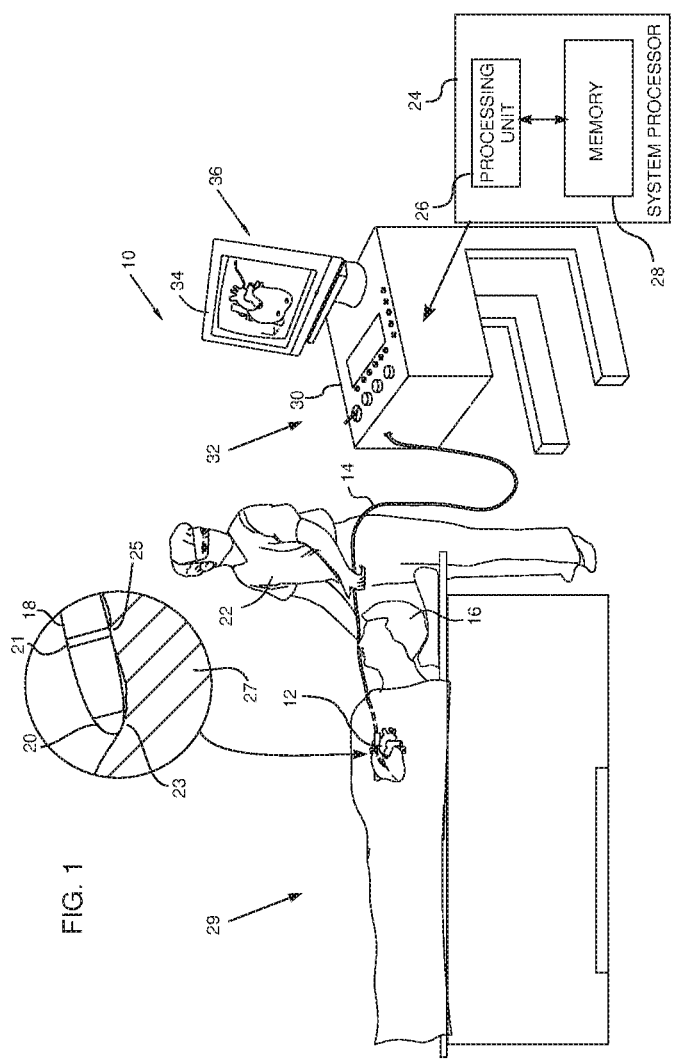
FIG. 1 is a schematic illustration of an activation time detection system, according to an embodiment of the present invention.

Reference is now made to FIG. 1, which is a schematic illustration of an activation time detection system 10, according to an embodiment of the present invention. System 10 analyzes electrocardiograph signals, in order to measure, inter alia, an onset point in time of a given signal. For simplicity and clarity, the following description, except where otherwise stated, assumes an investigative procedure wherein system 10 performs measurements on a heart 12, herein assumed to comprise a human heart, using a probe 14.

Typically, probe 14 comprises a catheter which is inserted into the body of a subject 16 during the investigative procedure. A distal tip 18 of the probe comprises a first electrode 20 and a second electrode 21 which receive electrocardiograph (ECG) signals from respective locations 23 and 25 in heart 12. The locations are typically within tissue 27 of the heart. The signals from the two electrodes form a bipolar signal which is analyzed by system 10, as described herein. The investigative procedure is performed by a user 22 of system 10, and in the description herein user 22 is assumed, by way of example, to be a medical professional.

One or more other electrodes 29 are used during the procedure. The other electrodes may be attached to probe 14, to another probe similar to probe 14 and located within the heart, and/or to the skin of subject 16. The other electrodes are used as reference electrodes to provide a reference ground for the signals from electrodes 20 and 21, in which case the two signals of the respective electrodes are unipolar signals.

System 10 is typically controlled by a system processor 24 which may be realized as a general purpose computer. The system processor comprises a processing unit 26 communicating with a memory 28. Processor 24 may be mounted in a console 30, comprising operating controls 32 that typically include a keypad and a pointing device such as a mouse or trackball that professional 22 uses to interact with the processor. Results of the operations performed by processor 24 are provided to the professional on a screen 34 which may display a diagram of the results of the analysis performed by the system. Alternatively or additionally, the results are used by system 10 in presenting other parameters to professional 22, such as a map of local activation times (LATs) of heart 12. Professional 22 is able to use controls 32 to input values of parameters used by processor 24 in the operation of system 10

Processor 24 uses software stored in memory 28 to operate system 10. The software may be downloaded to processor 24 in electronic form, over a network, for example, or it may, alternatively or additionally, be provided and/or stored on non-transitory tangible computer-readable media, such as magnetic, optical, or electronic memory.

System 10 can be realized as the CARTO XP EP Navigation and Ablation System, available from Biosense Webster, Inc., 3333 Diamond Canyon Road, Diamond Bar, Calif. 91765, suitably modified to execute the procedures described herein.

In some cases electrodes 20 and/or 21 may provide both ECG and other signals or the electrodes may be used for other purposes. For example, the CARTO system referenced above uses electrodes which detect ECG signals, measures impedances of the electrodes for tracking, as well as using the electrodes to provide radio-frequency ablation.

Figure 2:
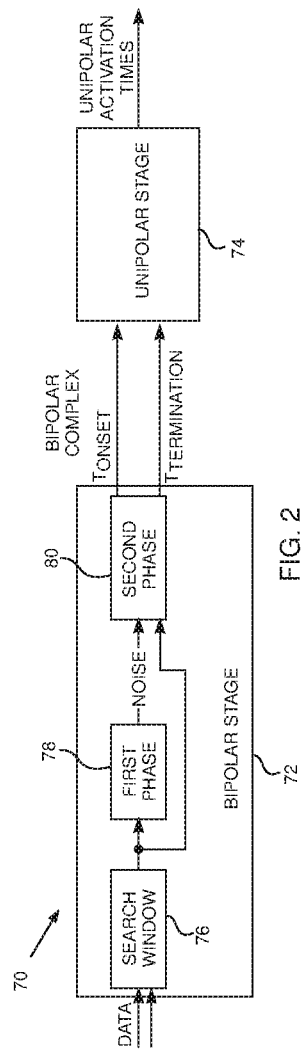
FIG. 2 is a schematic block diagram illustrating an overall process in operating the system, according to an embodiment of the present invention.

FIG. 2 is a schematic block diagram 70 illustrating an overall process followed by processor 24 in operating system 10, according to an embodiment of the present invention. In a bipolar stage 72, the processor receives raw unfiltered signals, as voltage levels, from electrodes 20 and 21 and operates on them to form bipolar signal data. The processor analyzes the bipolar data to determine a time period, or window, defining a bipolar complex. For simplicity and clarity, in the following description except where otherwise stated there is assumed to be one bipolar complex per heart beat.

The bipolar complex is bounded by an initial time instance $T_{ONSET}$ and a final time instance $T_{TERMINATION}$. The processor uses the time bounds of the bipolar complex to define a window within which to perform unipolar analysis.

In a unipolar stage 74, the processor considers each of the electrode 20 and 21 signals separately, as unipolar voltage vs. time signals, and analyzes the unipolar signals within the time window found in the bipolar stage. The analysis enables the processor to determine respective unipolar activation times at which the regions in contact with electrodes 20 and 21 activate. The activation times typically comprise times at which the derivative of the unipolar signal has a maximum negative value.

Bipolar stage 72 is formed of three modules: a search window module 76, and two subsequent modules, a first phase module 78 and a second phase module 80. The operations performed by the processor for each module are described below. In the description the signals from electrodes 20 and 21 are assumed to be sampled over a period of approximately 2.5 s at a rate of approximately 1 kHz, giving approximately 2,500 samples to be analyzed by system 10. However, system 10 may operate with any convenient sample period and rate of sampling.

Figure 3:
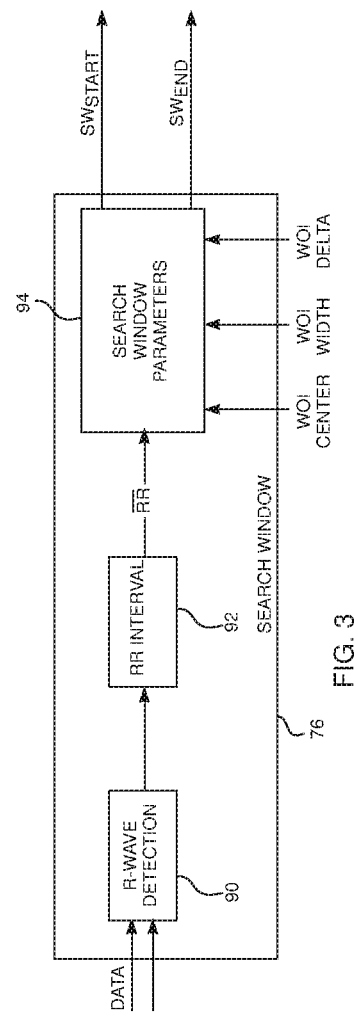
FIG. 3 is a schematic block diagram illustrating a search window module, according to an embodiment of the present invention.

FIG. 3 is a schematic block diagram illustrating search window module 76 in more detail, according to an embodiment of the present invention. In an R-wave detection block 90 processor 24 analyzes the set of incoming sample values to identify times at which the R-waves in the sample occurs. Typically for a set of samples taken over 2.5 s there are approximately two to four R-waves, although subjects having tachycardia may have five or more R-waves within a 2.5 s time period. The identification is typically performed by finding the times at which the sample peaks.

In an RR interval block 92 the processor finds the mean time periods $\overline{RR}$ between the peaks identified in block 92.

In a search window parameters block 94 the processor calculates times of a start and end times $SW_{START}$, $SW_{END}$, of a search window to be used in further analysis of the input data. In the CARTO system referenced above, professional 22 is able to program a window of interest (WOI) center time and width, $WOI_{CENTER}$, $WOI_{WIDTH}$. In order to perform the calculation in the CARTO system, block 94 uses values of parameters $WOI_{CENTER}$, $WOI_{WIDTH}$, together with an additional time period $WOI_{DELTA}$, also referred to herein using the symbol Δ, provided by professional 22. $WOI_{CENTER}$ is typically arbitrarily set by the professional to approximate an expected half-way point in time of mean time period $\overline{RR}$, but $WOI_{CENTER}$ may be set to be any other convenient point in time. $WOI_{WIDTH}$ is typically also arbitrarily set by the professional to approximate an expected mean time period but may also be set to any convenient time period. Using values of $WOI_{CENTER}$, $WOI_{WIDTH}$, and $WOI_{DELTA}$, block 94 calculates values of $SW_{START}$, $SW_{END}$ for the search window.

Figure 4:
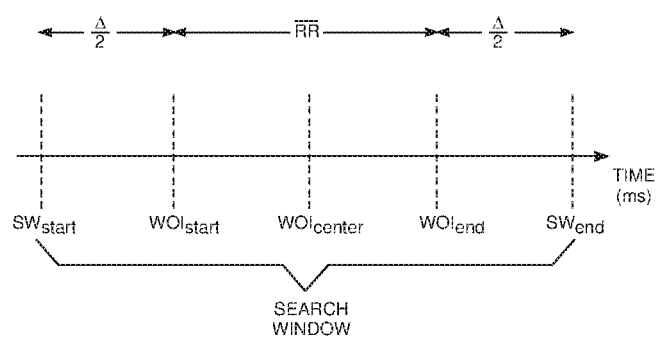
FIG. 4 is a time line illustrating a relationship between parameters used in a search window parameters block, according to an embodiment of the present invention.

FIG. 4 is a time line illustrating a relationship between the parameters used in search window parameters block 94, according to an embodiment of the present invention. As is illustrated by the time line, the search window delineated by block 94 has a total width of ($\overline{RR}+\Delta$), beginning at a time $SW_{START}$ and ending at a time $SW_{END}$.

It will be understood that while the calculation of the start and end times of the search window generated by block 94 has been explained with reference to the CARTO system, professional 22 may use any convenient method known in the art to delineate an appropriate search window.

A typical value for Δ is approximately 20 ms. A typical value of $\overline{RR}$ depends on subject 16. For a tachycardiac subject $\overline{RR}$ may be approximately 240 ms, in which case, with Δ=20 ms value, the search window is approximately 220 ms wide.

Figure 5:
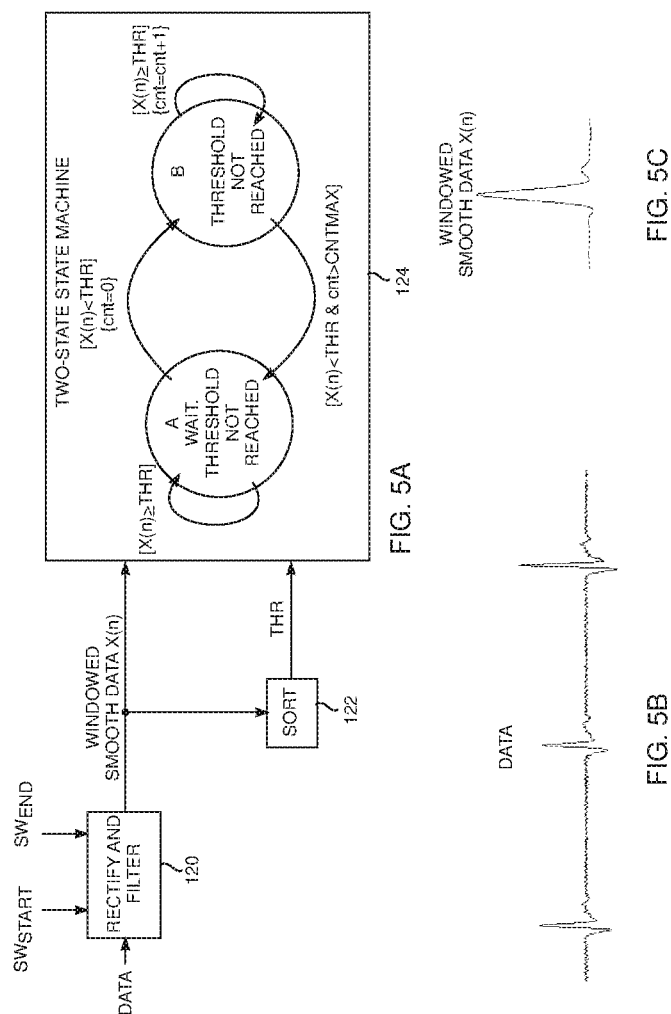
FIG. 5A is a schematic block diagram illustrating a first set of actions performed in a first phase block.
FIGS. 5B and 5C are schematic voltage vs. time graphs of data before and after the actions, according to embodiments of the present invention.

FIG. 5A is a schematic block diagram illustrating a first set of actions performed by processor 24 in first phase block 78, and FIGS. 5B and 5C are schematic voltage vs. time graphs of data before and after the actions, according to embodiments of the present invention. (For simplicity, voltage and time axes for the graphs are not shown.) In a rectify and filter block 120 bipolar raw data, from electrodes 20 and 21 and illustrated in FIG. 5B, is first rectified, then low-pass filtered to remove high frequency components from the data and to produce smoothed data. In one embodiment the inventors use a second order Butterworth filter having a cut off frequency of approximately 20 Hz.

The filtered smoothed data is then windowed, using the search window times $SW_{START}$ and $SW_{END}$ from block 94 (FIG. 3), to generate a set of sample data {X(n)} where n is an index of the data, and X is the data value. The set of smoothed data is schematically illustrated in FIG. 5C. Assuming the example search window width given above for a tachycardiac subject, and a sample rate of approximately 1000 Hz, there are approximately 220 smoothed samples in the windowed data, so that in this case n is a positive integer between 1 and approximately 220.

In a sort block 122 the smoothed samples are sorted by value and arranged into a frequency distribution. From the frequency distribution a threshold voltage level THR, that is to be applied in analyzing the data, is extracted. Level THR is selected to be close to, but above, the level of the smoothed baseline data. In one embodiment, the level is selected as a base value corresponding to the 5th percentile of the frequency distribution, added with a factor of 5% of the amplitude of the smoothed signal. Alternatively, level THR may be selected by any other suitable method for defining a level close to, but above, the smoothed baseline data.

In addition, sort block 122 determines a peak sample $X(n_{p1})$ of the smoothed data.

The processor supplies level THR, and the sampled smoothed values X(n) to a two-state state machine 124. Conditions for transitions between the two states A and B of the state machine are indicated in FIG. 5A within square brackets [ ]; actions performed during the transitions are indicated within braces { }. Starting from the peak sample $X(n_{p1})$, data X(n) are sequentially fed backward in time until a first transition, at an index underTHRstart, occurs. In addition the data are fed forward in time, starting from the peak sample $X(n_{p1})$, until a second transition, at an index underTHRend, occurs. A parameter cnt counts the number of samples operated on by the state machine. A user-set variable CNTMAX, indicative of an acceptable number of samples between transitions underTHRstart and underTHRend, is typically set to be approximately 100, but may be set to be any other convenient number.

Figure 6:
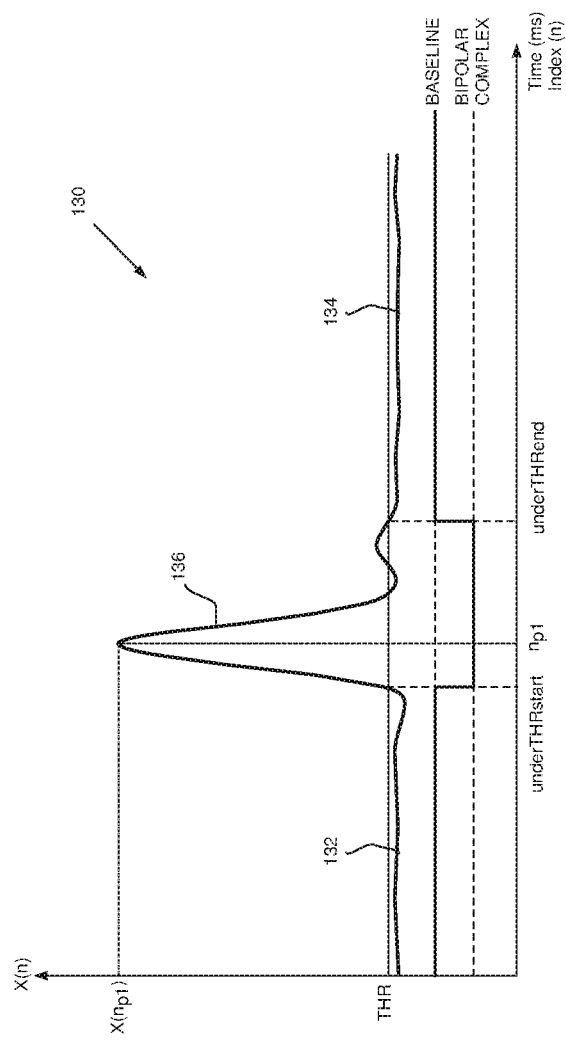
FIG. 6 illustrates windowed smoothed data output by a filter block, according to an embodiment of the present invention.

FIG. 6 illustrates the windowed smoothed data output by filter block 120 (as also shown schematically in FIG. 5C), according to an embodiment of the present invention. A graph 130 represents the windowed smoothed samples X(n) output by the filter block. State machine 124 divides the samples into three sections: two baseline sections 132 and 134 that are below threshold THR, and a bipolar complex section 136. The bipolar complex is bounded by the two transition indices underTHRstart and underTHRend generated by the state machine.

Figure 7:
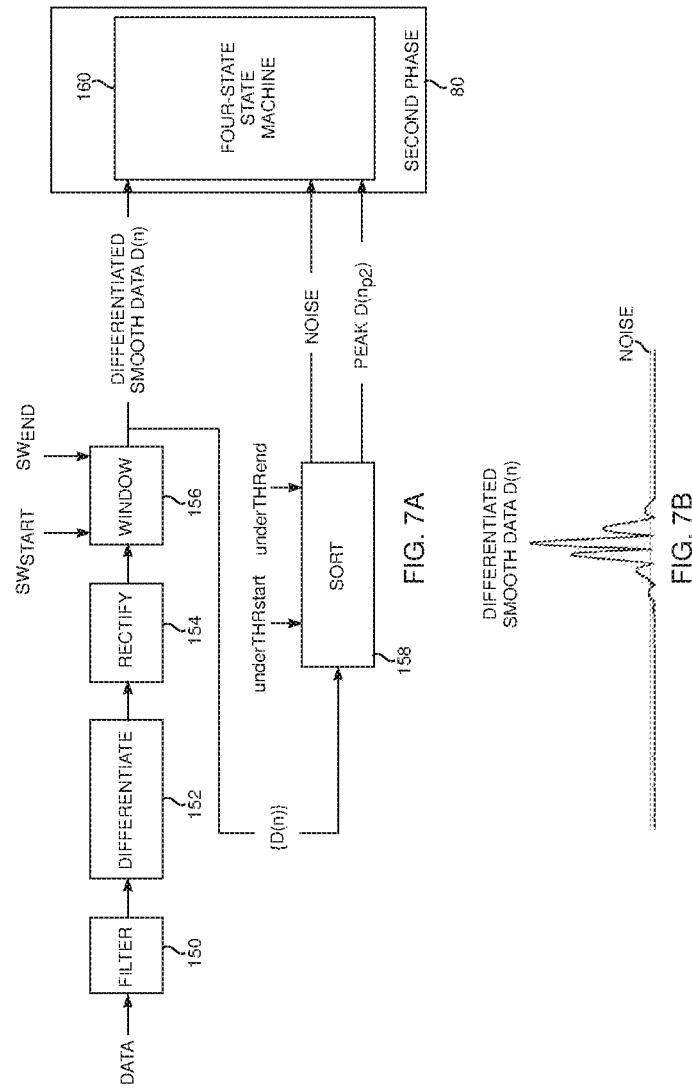
FIG. 7A is a schematic block diagram illustrating a second set of actions performed in the first phase block.
FIG. 7B is a schematic graph of data produced by the actions, according to embodiments of the present invention.

FIG. 7A is a schematic block diagram illustrating a second set of actions performed by processor 24 in first phase block 78 (FIG. 2), and FIG. 7B is a schematic graph of data produced by the actions, according to embodiments of the present invention. In a filter block 150, bipolar raw data from electrodes 20 and 21 is low-pass filtered to remove high frequency components and produce smoothed data. In one embodiment the inventors use a second order Butterworth filter having a cut off frequency of approximately 35 Hz. In a differentiation block 152 the smoothed data is differentiated, and is then rectified in a rectify block 154 to produce rectified differentiated data.

The data from block 154 is windowed in a window block 156, using the search window times $SW_{START}$ and $SW_{END}$ from block 94 (FIG. 3). The windowing generates a set of differentiated smooth data $\{D(n)\}$ where D is the data value. FIG. 7B is a graphic illustration of the data output of block 154, shown in more detail in FIG. 9.

The set of differentiated smooth data transfers to a sort block 158, as well as to a four-state state machine 160 in second phase 80 of the bipolar stage (FIG. 2). In sort block 158 the indices, underTHRstart and underTHRend, determined by two-state state machine 124 and illustrated in FIG. 6, are used to divide $\{D(n)\}$ into a differentiated binary complex section and two noise sections. Processor 24 sorts the values in both noise sections into a frequency distribution, and from the distribution a differentiated noise level NOISE, that is to be applied in analyzing the differentiated smooth data, is extracted. Level NOISE is selected to be close to, but above, the level of both noise sections, and is shown schematically in FIG. 7B. In one embodiment, the level is based on a 95th percentile of the frequency distribution.

Sort block 158 also determines a peak value $D(n_{p2})$ and an index $n_{p2}$ of the differentiated binary complex, and transfers $D(n_{p2})$ to the four-state state machine.

Figure 8:
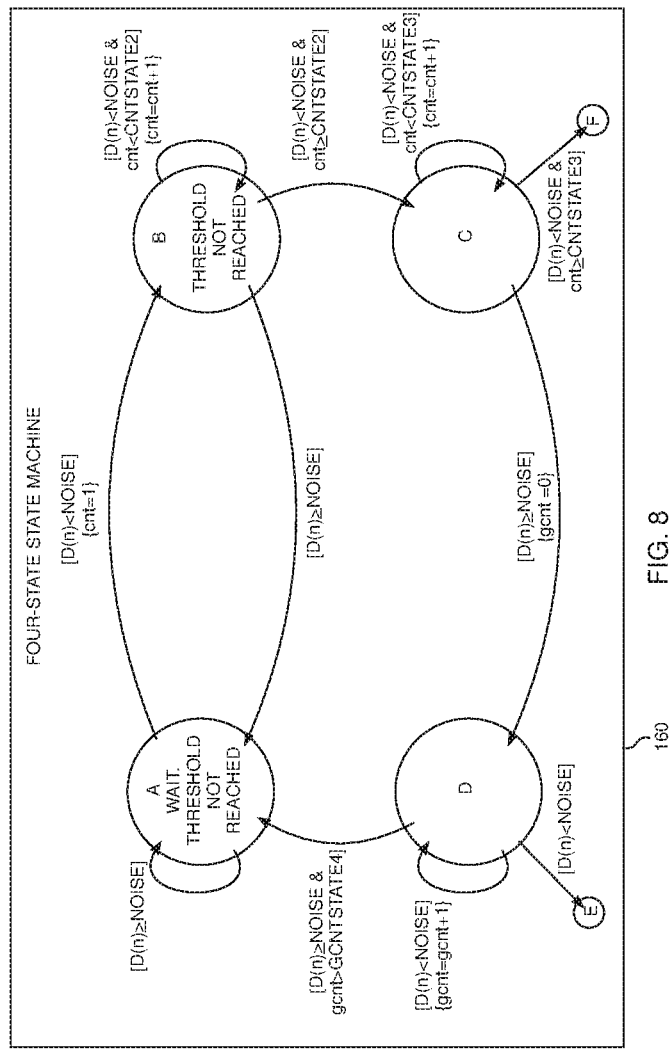
FIG. 8 is a schematic diagram of a four-state state machine, according to an embodiment of the present invention.

FIG. 8 is a schematic diagram of four-state state machine 160, according to an embodiment of the present invention. The state machine comprises four states A, B, C, and D, together with two exit states E end F. Conditions for transitions between the states are indicated in FIG. 8 within square brackets [ ]; actions performed during the transitions are indicated within braces { }. Starting from the peak sample $D(n_{p2})$, and with the state machine in state A, sample data D(n) are fed backward in time until exit state F is reached. The time, i.e., the index value, at which state F is reached is an onset time, $T_{ONSET}$, of the bipolar complex. In addition, a termination time, $T_{TERMINATION}$, of the bipolar complex is found by feeding sample data D(n) forward in time until exit state E is reached.

In the state machine, parameters cnt and gcnt count the number of samples operated on by the state machine. Variables CNTSTATE2, CNTSTATE3, and CNTSTATE4 may be set by professional 22, as representative of acceptable numbers of samples between states of the state machine as transitions occur through the differentiated noise level NOISE. Typical values of CNTSTATE2, CNTSTATE3, and CNTSTATE4 are respectively 8, 18, and 4, but the values may be set by professional 22 to any suitable value.

Figure 9:
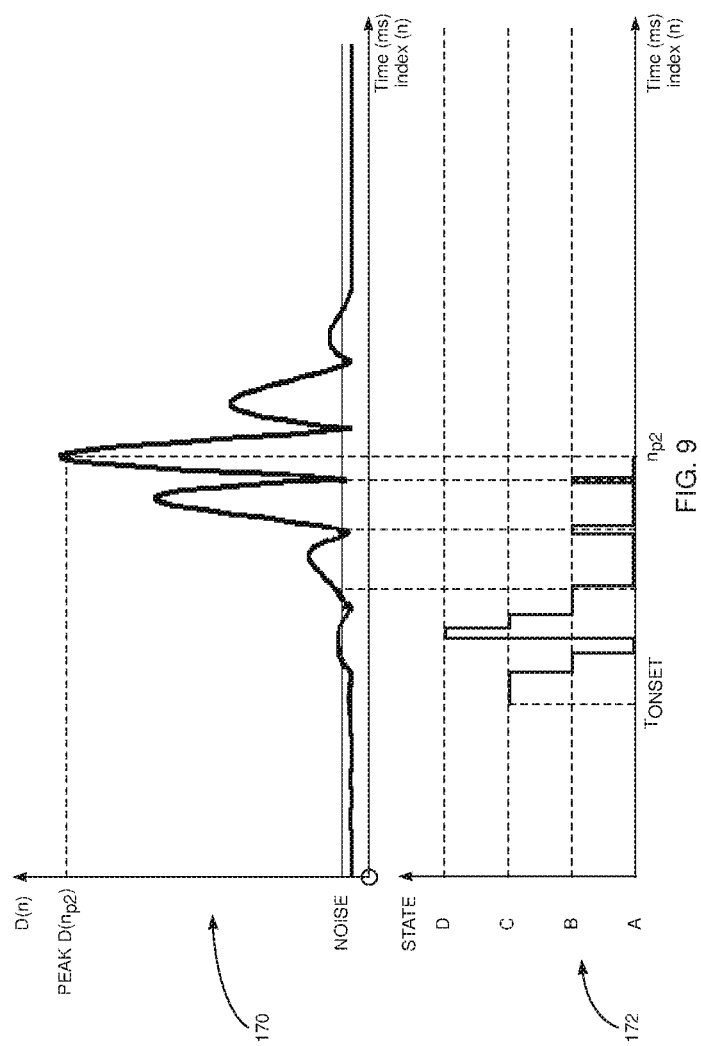
FIG. 9 illustrates the operation of the state machine, according to an embodiment of the present invention.

FIG. 9 illustrates the operation of state machine 160, according to an embodiment of the present invention. A graph 170 (similar to FIG. 7B) represents the smoothed data D(n) transferred from window block 156 to the state machine. Values of noise level NOISE, and PEAK $D(n_{p2})$, transferred from sort block 158, are also shown on graph 170.

A graph 172 shows the states of the state machine, and the transitions between the states, in determining the value of $T_{ONSET}$. As shown in the graph, processor 24 (FIG. 1) begins operating the state machine from the peak value $D(n_{p2})$, at sample $n_{p2}$, in state A. As succeeding backwards-in-time samples feed into the state machine, the machine, after initially alternating between states A and B, then transfers in turn to states C, D, A, B, and C. At the last state C, the machine transfers to exit state F (FIG. 8). A similar set of transitions occurs for samples fed forwards-in-time from peak value $D(n_{p2})$ the transitions ending in state D and exit state E and determining the value of $T_{TERMINATION}$.

Figure 10:
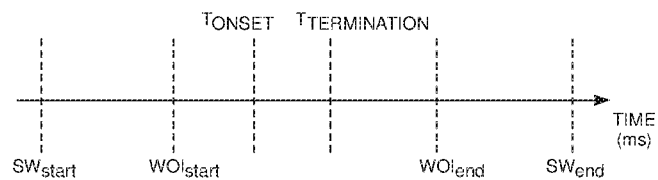
FIG. 10 illustrates values of time instances plotted on a time line, according to an embodiment of the present invention.

FIG. 10 illustrates values of $T_{ONSET}$ and $T_{TERMINATION}$ plotted on a time line, according to an embodiment of the present invention. The time line illustrates a typical relationship between the values of $T_{ONSET}$ and $T_{TERMINATION}$ and the time values used in investigating the bipolar complex and described above with reference to FIG. 4.

From the values of $T_{ONSET}$ and $T_{TERMINATION}$ system 10 is able to evaluate a signal-to-noise ratio (SNR) of the bipolar complex, according to equation (1):

$$SNR = 20 \cdot \log\left(\frac{S-N}{N}\right) \quad (1)$$

where S is the root mean square (RMS) value of the unfiltered bipolar data lying between $T_{ONSET}$ and $T_{TERMINATION}$, and N is the RMS value of the unfiltered bipolar data before $T_{ONSET}$ and after $T_{TERMINATION}$.

Professional 22 is able to use the value of SNR in order to establish a confidence level for the evaluated values of $T_{ONSET}$ and $T_{TERMINATION}$.

Returning to FIG. 2, processor 24 transfers the values of $T_{ONSET}$ and $T_{TERMINATION}$ to unipolar stage 74. In stage 74, the processor forms a time window, bounded by $T_{ONSET}$ and $T_{TERMINATION}$, and analyzes the smoothed unipolar voltage (V) vs. time (t) signals from each of electrodes 20 and 21 within the window. Within the window the processor calculates values of the slopes of each unipolar signal, i.e., values of first derivative $$\frac{dV}{dt}.$$

For each signal the processor selects the time at which the first derivative $$\frac{dV}{dt}$$

has its most negative, i.e., its minimum, value, and this time is assumed to be the time at which the tissue generating the signal begins to activate.

Figure 11A:
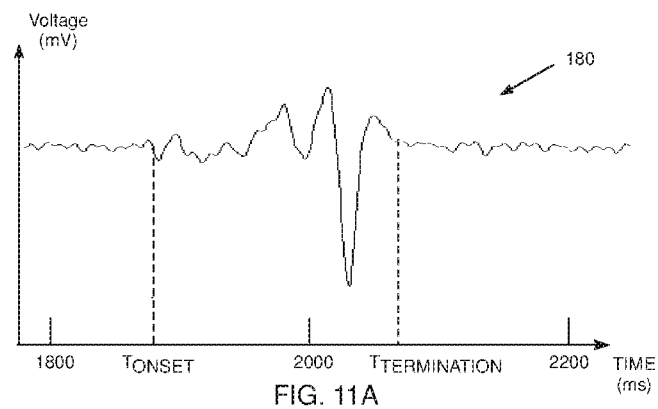
FIGS. 11A and 11B are schematic bipolar and unipolar graphs, according to an embodiment of the present invention.
Figure 11B:
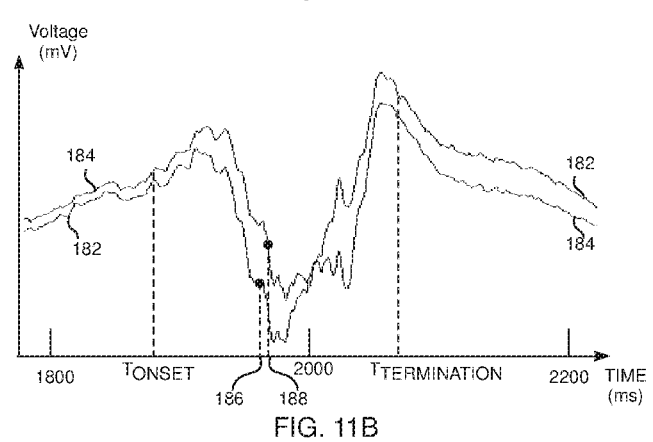

FIGS. 11A and 11B are schematic bipolar and unipolar graphs, according to an embodiment of the present invention. A graph 180 is a voltage vs. time graph of a bipolar signal, and graphs 182 and 184 are voltage vs. time graphs of respective unipolar signals forming the bipolar signal. Both sets of graphs have times $T_{ONSET}$ and $T_{TERMINATION}$, as determined above, marked on the graphs. In the case of graphs 182 and 184, respective activation times 186 and 188, being the times of the most negative derivative of the respective unipolar signals within the window defined by $T_{ONSET}$ and $T_{TERMINATION}$, are shown. Activation times 186 and 188 are the times that the tissue generating the unipolar signals begins to activate, and are also herein termed unipolar onset activation times.

For clarity, the description above considers embodiments of system 10 that evaluate signal parameters where there is one bipolar complex per heart beat. System 10 is not limited to such evaluations, and may be used to identify signals where multiple bipolar complexes occur per heart beat, and furthermore, to evaluate signal parameters of the multiple bipolar complexes. The identification of the occurrence of multiple bipolar signals may typically be by measuring intervals between adjacent complexes, since, in contrast to signals having one bipolar complex per heart beat, the intervals change. Those having ordinary skill in the art will be able to adapt the description above, mutatis mutandis, to evaluate parameters of unipolar signals generating multiple bipolar complexes occur per heart beat. Such parameters include, but are not limited to, evaluating respective unipolar onset activation times for each bipolar complex in a given heart beat.

Figure 12A:
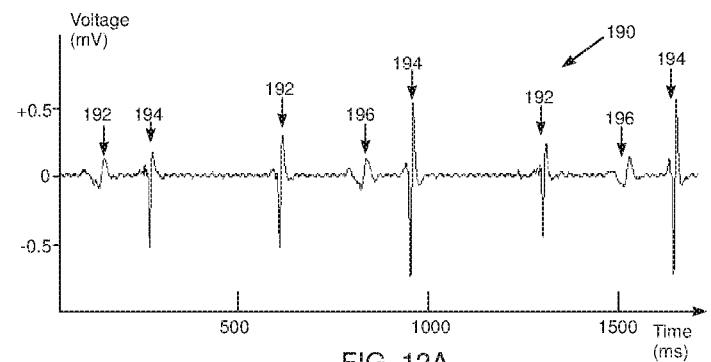
FIGS. 12A, 12B, and 12C are graphs of signals derived from multiple bipolar complexes occurring within one heart beat, according to embodiments of the present invention.
Figure 12B:
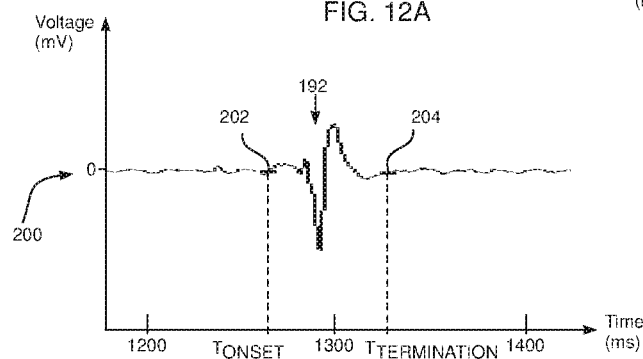
Figure 12C:
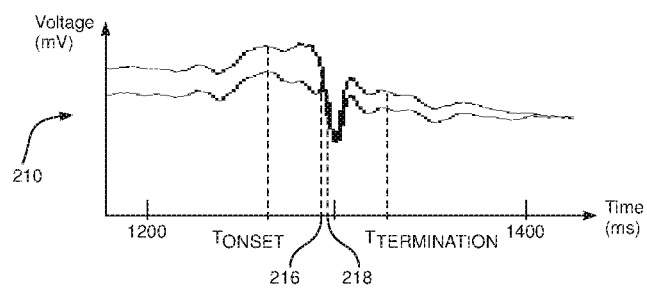

FIGS. 12A, 12B, and 12C are graphs of signals derived from multiple bipolar complexes occurring within one heart beat, according to embodiments of the present invention. A graph 190 (FIG. 12A) is a bipolar signal exhibiting an atrial bipolar complex 194, and ventricular bipolar complexes 192 and 196. Each bipolar complex may be analyzed by initially defining a search window for a given complex. A method for defining the search window for each complex is substantially as described above with reference to FIG. 3, mutatis mutandis, to allow for differing RR intervals within the bipolar signal.

A graph 200 (FIG. 12B) is an enlarged graph of a specific ventricular bipolar complex 192. Onset and termination times 202 and 204 for the complex have been marked on the graph. The times are evaluated substantially as described above with reference to FIG. 8, by feeding smoothed data derived from the complex through state machine 160.

A graph 210 (FIG. 12C) illustrates unipolar signals 212 and 214 corresponding to bipolar complex 192 of FIG. 12B. As described above, respective unipolar onset activation times 216 and 218 for each signal, occur at the times wherein the first derivative of each signal, measured between onset and termination times 202 and 204, has its most negative value, i.e., is a minimum.

System 10 may also be used to evaluate other parameters relevant to signals having multiple bipolar complexes occurring within one heart beat, as will be apparent to those of ordinary skill in the art. Such parameters include, but are not limited to, a duration time between first and second atrial bipolar complexes, by measuring a mean RR interval between the complexes. All such parameters are assumed to be included within the scope of the present invention.

Figure 13:
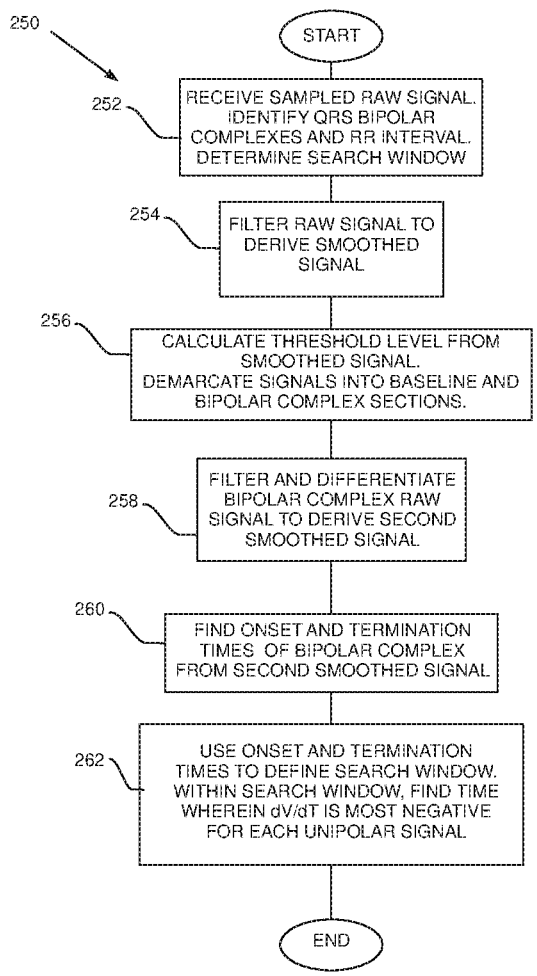
FIG. 13 is a flowchart of steps followed to determine activation times, according to an embodiment of the present invention.

FIG. 13 is a flowchart 250 of steps followed by processor 24 in operating system 10 to determine activation times, according to an embodiment of the present invention. For simplicity and clarity, the description of the steps of the flowchart assumes that signals received have one bipolar complex per heart beat, except where otherwise stated. Those with ordinary skill in the art will be able to adapt the description for cases having multiple bipolar complexes per heart beat.

Steps 252-260 are actions performed in bipolar stage 72 and step 262 is performed in unipolar stage 74 (FIG. 2).

In an initial step 252, the processor receives signals as sampled data from electrodes 20 and 21. The processor analyzes the signals to identify R waves, an $\overline{RR}$ value, and bounds of a search window, as described above with reference to FIGS. 3 and 4.

In a first filtration step 254, the sampled data are rectified, filtered, and windowed, and the resulting smoothed data is fed into two-state state machine 124. In a demarcation step 256 the two-state state machine divides the data it receives into baseline sections and a bipolar complex section. Steps 254 and 256 are as described above with reference to FIGS. 5A-5C and FIG. 6.

In a second filtration step 258, the sampled data of the bipolar complex are filtered, differentiated and windowed to derive a second smoothed signal, as described above with reference to FIGS. 7A and 7B.

In a bipolar complex analysis step 260, the processor evaluates onset and termination times of the complex by feeding the second smoothed signal data into four-state state machine 160, as described with reference to FIGS. 8 and 9.

In an activation time step 262, a time of activation of tissue in contact with electrodes 20 and 21 is determined by analyzing the unipolar signals from each electrode within a window defined by the bipolar onset and termination times of step 260. Actions performed by the processor in step 262 are described with reference to FIGS. 11A and 11B, and also (for situations of multiple bipolar complexes in one heart beat) with reference to FIGS. 12A-12C.

The analysis differentiates the unipolar signals within the window, and finds the respective times at which the first derivatives are most negative, i.e., are minima. These times correspond to an onset activation time of the tissue in contact with electrode 20, and an onset activation time of the tissue in contact with electrode 21.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for characterizing an electrocardiogram, comprising:
receiving a first unipolar signal from a first location of a heart and a second unipolar signal from a second location of the heart said first unipolar signal and said second unipolar signal comprising raw unfiltered signals;
generating a bipolar signal from the first and second unipolar signals;
analyzing the bipolar signal to delineate a time period during which the first and second locations generate a bipolar complex whereby analyzing the bipolar signal includes determining search window bounds to be applied to the bipolar signal,
rectifying and filtering the bipolar signal to produce smooth data,
windowing the filtered smooth data to generate a set of sample data,
sorting the sample of smooth data by value into sample smoothed values and into a frequency distribution,
extracting a threshold voltage level from the frequency distribution and supplying the threshold voltage level and the sample smoothed values into a two-state state machine so as to determine bounds of the time period; and
analyzing the first unipolar signal by applying the search window bounds to the first unipolar signal to determine an activation time of the first location.

2. The method according to claim 1, wherein analyzing the bipolar signal comprises rectifying data of the bipolar signal and differentiating the rectified data of the bipolar signal, so as to generate differentiated data.

3. The method according to claim 1, wherein determining the activation time comprises forming a first derivative of the first unipolar signal, and assigning a unipolar onset activation time as a time instant wherein the first derivative is a minimum value.

4. The method according to claim 1, wherein the activation time comprises a first activation time, the method further comprising analyzing the second unipolar signal within the time period to determine a second activation time of the second location.

5. The method according to claim 1, wherein the bipolar complex comprises a first bipolar complex and a second bipolar complex, and wherein the time period comprises a first time period during which the first bipolar complex is generated and a second time period during which the second bipolar complex is generated, and wherein analyzing the first unipolar signal comprises determining first and second activation times respectively within the first and second time periods.

6. Apparatus for characterizing an electrocardiogram, comprising:
a probe which is configured to receive a first unipolar signal from a first location of a heart and a second unipolar signal from a second location of the heart said first unipolar signal and said second unipolar signal comprising raw unfiltered signals; and
a processor which is configured to:
generate a bipolar signal from the first and second unipolar signal,
analyze the bipolar signal data to delineate a time period during which the first and second locations generate a bipolar complex and rectifying and filtering the bipolar signal to produce smooth data, windowing the filtered smooth data to generate a set of sample data, sorting the sample of smooth data by value into sample smoothed values and into a frequency distribution, extracting a threshold voltage level from the frequency distribution and supplying the threshold voltage level and the sample smoothed values into a two-state state machine so as to determine bounds of the time period, and
analyze the first unipolar signal within the time period to determine an activation time of the first location.

7. The apparatus according to claim 6, wherein analyzing the bipolar signal comprises determining search window bounds to be applied to the bipolar signal.

8. The apparatus according to claim 6, wherein analyzing the bipolar signal comprises rectifying data of the bipolar signal and differentiating the rectified data of the bipolar signal, so as to generate differentiated data.

9. The apparatus according to claim 6, wherein determining the activation time comprises forming a first derivative of the first unipolar signal, and assigning a unipolar onset activation time as a time instant wherein the first derivative is a minimum value.

10. The apparatus according to claim 9, wherein the activation time comprises a first activation time, and further comprising analyzing the second unipolar signal within the time period to determine a second activation time of the second location.

11. The apparatus according to claim 6, wherein the bipolar complex comprises a first bipolar complex and a second bipolar complex, and wherein the time period comprises a first time period during which the first bipolar complex is generated and a second time period during which the second bipolar complex is generated, and wherein analyzing the first unipolar signal comprises determining first and second activation times respectively within the first and second time periods.

12. A computer software product for characterizing an electrocardiogram, including a tangible non-transitory computer-readable medium in which computer program instructions are stored, which instructions, when read by a computer, cause the computer to:
receive a first unipolar signal from a first location of a heart and a second unipolar signal from a second location of the heart said first unipolar signal and said second unipolar signal comprising raw unfiltered signals;
receiving the raw unfiltered signals and operating on the raw and unfiltered signals to form a bipolar signal data;
analyze the bipolar signal to delineate a time period during which the first and second locations generate a bipolar complex, rectifying and filtering bipolar signal raw data to produce smooth data, windowing the filtered smooth data to generate a set of sample data, sorting the sample of smooth data by value into sample smoothed values and into a frequency distribution, extracting a threshold voltage level from the frequency distribution and supplying the threshold voltage level and the sample smoothed values into a two-state state machine so as to determine bounds of the time period; and
analyze the first unipolar signal within the time period to determine an activation time of the first location.

* * * * *